US008831712B2

(12) United States Patent
Hayashi et al.

(10) Patent No.: US 8,831,712 B2
(45) Date of Patent: Sep. 9, 2014

(54) ELECTROCARDIOGRAM ANALYZER AND ELECTRODE SET

(71) Applicant: Nihon Kohden Corporation, Tokyo (JP)

(72) Inventors: Satoshi Hayashi, Tokyo (JP); Tsutomu Wakabayashi, Tokyo (JP); Hideo Ozawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 14/029,223

(22) Filed: Sep. 17, 2013

(65) Prior Publication Data

US 2014/0100466 A1    Apr. 10, 2014

(30) Foreign Application Priority Data

Oct. 9, 2012 (JP) ................................. 2012-224456

(51) Int. Cl.
*A61B 5/04* (2006.01)
*A61B 5/00* (2006.01)
*A61N 1/39* (2006.01)
*A61B 5/046* (2006.01)
*A61B 5/053* (2006.01)

(52) U.S. Cl.
CPC ........... *A61B 5/04012* (2013.01); *A61B 5/7282* (2013.01); *A61N 1/39* (2013.01); *A61B 5/046* (2013.01); *A61B 5/721* (2013.01); *A61B 5/053* (2013.01)
USPC .............................................. 600/509; 607/5

(58) Field of Classification Search
USPC .............................................. 600/509; 607/5
See application file for complete search history.

(56) References Cited

U.S. PATENT DOCUMENTS

| 6,546,285 | B1 * | 4/2003 | Owen et al. ................... 607/5 |
| 2003/0109790 | A1 | 6/2003 | Stickney et al. |
| 2005/0256415 | A1 | 11/2005 | Tan et al. |
| 2006/0011203 | A1 | 1/2006 | Myklebust |
| 2008/0027339 | A1 | 1/2008 | Nagai et al. |
| 2011/0105930 | A1 | 5/2011 | Thiagarajan et al. |

FOREIGN PATENT DOCUMENTS

| EP | 1 491 176 A1 | 12/2004 |
| EP | 2 319 409 A1 | 5/2011 |
| JP | 2011-189139 A | 9/2011 |
| JP | 4830857 B2 | 12/2011 |
| WO | 2006006871 A2 | 1/2006 |

OTHER PUBLICATIONS

Elaine Fitzgibbon, MSE et al.; "Determination of the noise source in the electrocardiogram during cardiopulmonary resuscitation"; Lippincott Williams & Wilkins; Crit Care Med 2002, vol. 30, No. 4, pp. 148-153.
The extended European Search Report for the related European Patent Application No. 13185471.3 dated Jan. 3, 2014.

* cited by examiner

*Primary Examiner* — Nicole F Lavert
(74) *Attorney, Agent, or Firm* — Kenealy Vaidya LLP

(57) ABSTRACT

An electrocardiogram analyzer includes: one set of electrocardiogram measurement electrodes; one or more noise measurement electrode; a measurer which is configured to measure an electrocardiogram signal acquired by the electrocardiogram measurement electrodes, and a noise signal acquired by at least the noise measurement electrode; and an electrocardiogram extraction analyzer which is configured to extract a noise-removed electrocardiogram in which noise is removed, based on the electrocardiogram signal and the noise signal.

15 Claims, 10 Drawing Sheets

ELECTROCARDIOGRAM ANALYZER AND ELECTRODE SET

CROSS-REFERENCE TO RELATED APPLICATION(S)

This application is based upon and claims the benefit of priority from prior Japanese patent application No. 2012-224456, filed on Oct. 9, 2012, the entire contents of which are incorporated herein by reference.

BACKGROUND

The presently disclosed subject matter relates to an electrocardiogram analyzer and electrode set in which the influence of noise caused by the cardiopulmonary resuscitation (hereinafter, abbreviated as CPR) can be reduced.

As a life-saving measure for a patient in cardiac arrest, it is important to constantly perform chest compression. For a cardiac arrest patient who experiences ventricular fibrillation or pulseless ventricular tachycardia, delivery of electric shock constitutes an important factor. In order to rapidly perform adequate procedures on such a patient, therefore, an analytically accurate measurement of an electrocardiogram is necessary even during chest compression. When chest compression is performed on a patient in cardiac arrest, however, noise contaminates an electrocardiogram, and impedes analyzing of the electrocardiogram.

Non-patent Document 1 below reports that the noise contamination is not caused by deformation of the heart or a change of the chest impedance due to the compression, but by a disturbance which is applied between an electrode and the skin. Moreover, a disturbance which is applied between an electrode and the skin during chest compression changes in various factors such as the strength and rate of the compression, characteristics of the electrode, and the condition of the portion to which the electrode is bonded (the muscle and fat masses, and the dry condition of the skin). Therefore, noise appears unevenly in an electrocardiogram, and hence it is difficult to obtain an adequate analysis result from an electrocardiogram contaminated with noise.

Therefore, Patent Document 1 below proposes a technique in which features in the frequency region of single or plural electrocardiogram leads are analyzed, thereby determining whether electric shock is necessary or not, irrespective of the presence or absence of noise caused by chest compression.

Patent Document 2 below discloses a filtering technique which is based on detection of pulses (beats of the heart) contained in an electrocardiogram. In this technique, a baseline variation between pulses is captured, and the cutoff frequency band of a low-cut filter is changed, thereby removing noise. This technique can be applied also to noise contamination due to chest compression.

(Patent Document 1) JP-A-2011-189139
(Patent Document 2) Japanese Patent No. 4,830,857
(Non-patent Document 1) Determination of the noise source in the electrocardiogram during cardiopulmonary resuscitation, Crit Care Med 2002 Vil. 30, No. 4

In noise caused by chest compression, however, peaks appear not only at the frequency corresponding to the rate of the chest compression, but also at frequencies which are integer multiples of the frequency. Therefore, there is a possibility that the determination may not be correctly performed by the technique disclosed in Patent Document 1. For example, the rate of chest compression which is recommended in the guidelines is 100 times/minute. In this case, peaks appear at the fundamental period of 1.67 Hz, and also at integer multiple frequencies such as 3.33 Hz which is twice the period, and 5.0 Hz which is thrice the period. On the other hand, the frequency of ventricular fibrillation is about 2 to 10 Hz. The above-mentioned twice and thrice frequencies are within the range. Even when the fundamental period is removed by a low-cut filter, therefore, there is a possibility that peaks appearing at integer multiples of the fundamental period may affect the result of feature analysis.

The technique disclosed in Patent Document 2 has an advantage that the cut-off band can be changed in accordance with contaminating noise. However, there is a possibility that, when the cut-off band of the low-cut filter is set to be extremely high, even components of an electrocardiogram may be removed. Moreover, the technique is based on detection of the QRS wave indicating the beat of the heart. Therefore, the filtering process does not properly function in the case of ventricular fibrillation or cardiac arrest in which a beat does not exist.

SUMMARY

The presently disclosed subject matter may provide an electrocardiogram analyzer and electrode set in which an effective analyzing process is performed on an electrocardiogram during a rescue procedure by the intended CPR, whereby the influence of noise caused by the CPR can be reduced.

The electrocardiogram analyzer may comprise: one set of electrocardiogram measurement electrodes; one or more noise measurement electrode; a measurer which is configured to measure an electrocardiogram signal acquired by the electrocardiogram measurement electrodes, and a noise signal acquired by at least the noise measurement electrode; and an electrocardiogram extraction analyzer which is configured to extract a noise-removed electrocardiogram in which noise is removed, based on the electrocardiogram signal and the noise signal.

The set of electrocardiogram measurement electrodes may be a pair of defibrillation pads adapted to apply electric shock.

The noise measurement electrode may include a pair of defibrillation pads adapted to apply electric shock.

The noise measurement electrode may include an electrode which is placed in a vicinity of corresponding one of the electrocardiogram measurement electrodes.

The noise measurement electrode may be disposed in an opening formed in corresponding one of the electrocardiogram measurement electrodes.

The noise measurement electrode may be placed between the set of electrocardiogram measurement electrodes.

The noise signal may be a signal which is acquired between one set of the noise measurement electrodes, or between the noise measurement electrode and the electrocardiogram measurement electrodes.

The noise signal may be based on an impedance which is acquired when a carrier current is applied between one set of the noise measurement electrodes, or an impedance which is acquired when a carrier current is applied between the noise measurement electrode and the electrocardiogram measurement electrodes.

A period of chest compression may be obtained from the noise signal, and a filtering process may be performed based on a frequency of the chest compression.

An adaptive filtering process in which the noise signal is used as a reference may be performed.

A filtering process may be performed on the noise signal and the electrocardiogram signal by independent component analysis.

Cables for the electrocardiogram measurement electrodes, and at least one cable for the noise measurement electrode may be attached to one connector, and the connector may be connectable to the measurer.

Cables for the electrocardiogram measurement electrodes, and at least one cable for the noise measurement electrode may be distributively attached to two or more connectors, and the connectors may be connectable to the measurer.

One of the electrocardiogram measurement electrodes, and the noise measurement electrode may be disposed on one sheet, and be connectable to the measurer.

The electrocardiogram measurement electrodes, and the noise measurement electrode may be distributively disposed on at least two sheets, and be connectable to the measurer.

The electrocardiogram analyzer may be incorporated in a defibrillator.

The electrode set which is to be connected to an external apparatus may comprise: one set of electrocardiogram measurement electrodes; one or more noise measurement electrode; a measurer which is configured to measure an electrocardiogram signal acquired by the electrocardiogram measurement electrodes, and a noise signal acquired by at least the noise measurement electrode; an electrocardiogram extraction analyzer which is configured to extract a noise-removed electrocardiogram in which noise is removed, based on the electrocardiogram signal and the noise signal; and a transmitter which is configured to transmit the noise-removed electrocardiogram to the external apparatus.

BRIEF DESCRIPTION OF THE DRAWINGS

FIG. 3A shows the signal of lead Pad, FIG. 3B shows the signal of lead N1, and FIG. 3C shows the signal of lead N2.

FIG. 4A shows the signal of lead Pad, FIG. 4B shows the signal of lead N1, and FIG. 4C shows the signal of lead N2.

FIG. 12A shows the signal of lead Pad in which ventricular fibrillation is contaminated with noise, FIG. 12B shows a reference waveform indicating the difference between signals of leads N1 and N2 which are noise signals, and FIG. 12C shows a true ECG in which noise is removed by the adaptive filtering.

DETAILED DESCRIPTION OF EXEMPLARY EMBODIMENTS

Hereinafter, an example of an embodiment of the electrocardiogram analyzer of the presently disclosed subject matter will be described with reference to the accompanying drawings.

First Embodiment

Figure 1:
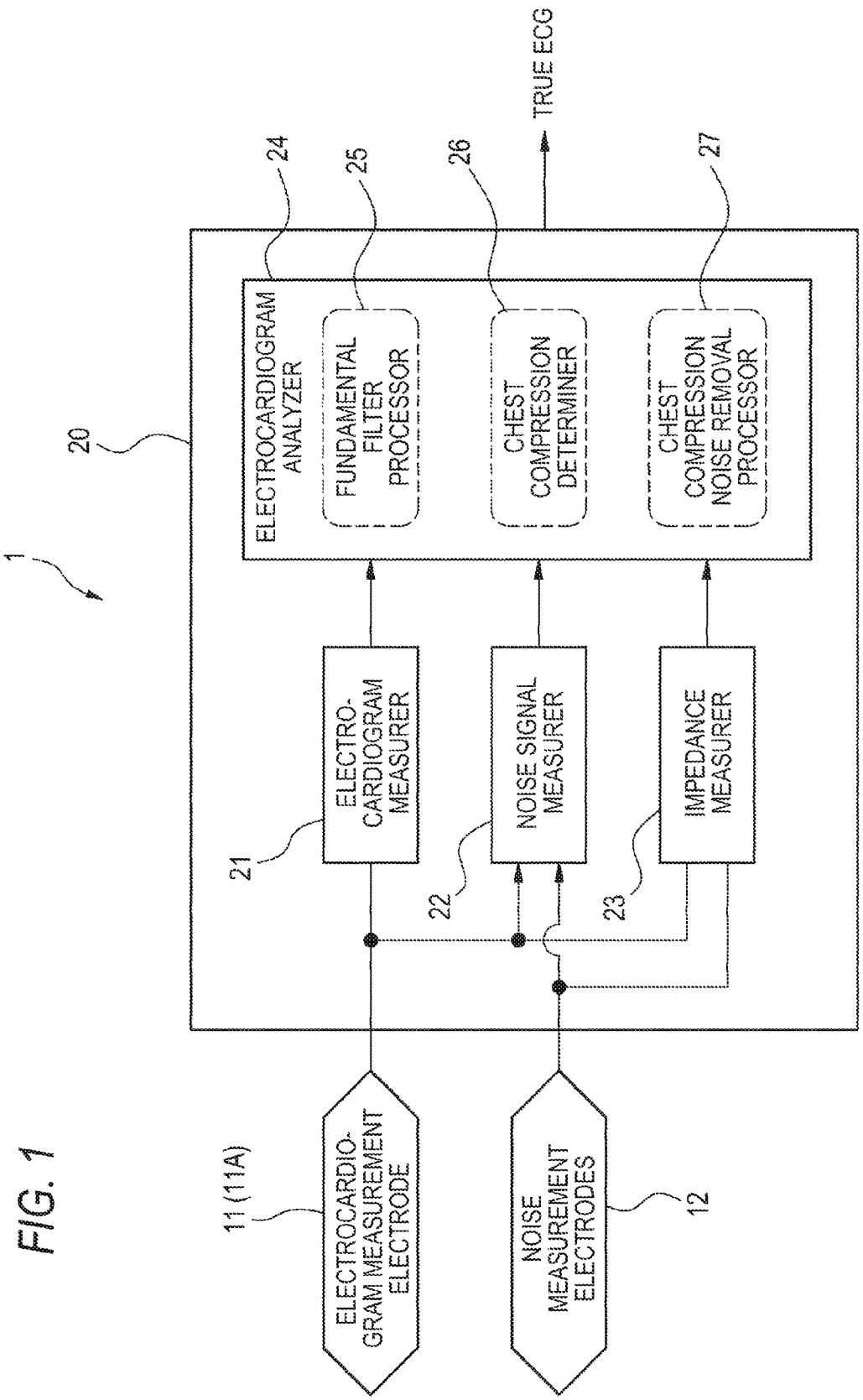
FIG. 1 is a block diagram showing an example of the function and configuration of the electrocardiogram analyzer of the presently disclosed subject matter.

FIG. 1 shows the configuration of an electrocardiogram analyzer 1 of a first embodiment. As the first embodiment, the electrocardiogram analyzer 1 which is used in a defibrillator will be described.

The electrocardiogram analyzer includes the electrocardiogram analyzer main unit 20, and electrocardiogram measurement electrodes 11 and noise measurement electrodes 12 which are to be attached to the patient (living body). The electrocardiogram analyzer main unit 20 includes: an electrocardiogram measurer 21 (an example of a measurer) to which the electrocardiogram measurement electrodes 11 are connected; a noise signal measurer 22 (an example of the measurer) to which the electrodes 11 and the noise measurement electrodes 12 are connected; an impedance measurer 23 (an example of the measurer) to which the electrocardiogram measurement electrodes 11 and the noise measurement electrodes 12 are connected; and an electrocardiogram analyzer 24 which extracts a true electrocardiogram (noise-removed electrocardiogram) in which noise is removed based on information measured by the measurers 21, 22, 23. The electrocardiogram analyzer 24 includes a fundamental filter processor 25, a chest compression determiner 26, and a chest compression noise removal processor (an example of an electrocardiogram extraction analyzer) 27.

The electrocardiogram measurement electrodes 11 are electrodes which are used for measuring an electrocardiogram (hereinafter, abbreviated as ECG) of the patient, and for example may be configured by defibrillation pads for applying electric shock.

The noise measurement electrodes 12 are electrodes which are used for measuring a noise signal, and for example may be used for measuring a noise signal due to a disturbance which is applied when the CPR, particularly chest compression is performed. As the noise measurement electrodes 12, at least one electrode may be disposed. In the embodiment, one set of two electrodes is disposed as the noise measurement electrodes.

The electrocardiogram measurer 21 measures an electrocardiogram acquired by the electrocardiogram measurement electrodes 11. In the case where chest compression is performed on the patient, the waveform of the electrocardiogram acquired in this case contains a mixture of a potential change caused by the heart, and that caused by the chest compression. Hereinafter, the potential change caused by the heart is referred as "true ECG", and the potential change caused by the chest compression is referred as "noise". Namely, the true ECG means the electrocardiogram waveform in which noise is removed.

The noise signal measurer 22 measures noise signals acquired by the electrocardiogram measurement electrodes 11 and the noise measurement electrodes 12. Here, noise signals mean a signal indicating a feature of noise which is caused to contaminate the electrocardiogram by the chest compression. When considered as a potential change, namely, the noise signals are signals containing only the potential change caused by the chest compression, or that containing an electric signal caused by the chest compression, and another electric signal which is sufficiently smaller than the potential change caused by the chest compression, and which is caused by the heart. The noise signals are acquired between the one set of noise measurement electrodes 12, or between the noise measurement electrodes 12 and the electrocardiogram measurement electrodes 11. In the electrocardiogram analyzer 1 of the presently disclosed subject matter, by using the noise signals, noise can be reduced from the electrocardiogram which is contaminated with noise by chest compression.

The impedance measurer 23 measures the inter-electrode chest impedance acquired by the electrocardiogram measurement electrodes 11 and the noise measurement electrodes 12. The chest impedance is changed by performing chest compression. Therefore, a measurement value of the chest impedance can be treated as one kind of noise signals. The noise signals can be measured by, when a carrier current is applied between the one set of noise measurement electrodes 12, or between the noise measurement electrodes 12 and the electrocardiogram measurement electrodes 11, measuring the chest impedance acquired from the electrodes.

The electrocardiogram analyzer 24 includes the fundamental filter processor 25, the chest compression determiner 26, and the chest compression noise removal processor 27.

On the electrocardiogram and the noise signals, the fundamental filter processor 25 performs processes such as removal of AC components by a hum filter, that of drift components by a high-pass filter, and that of high-frequency components which may enter from peripheral apparatuses and the like, by a low-pass filter.

The chest compression determiner 26 determines whether chest compression is performed on the patient or not, based on a change of the chest impedance measured by the impedance measurer 23, and the noise signals measured by the noise signal measurer 22. During chest compression, for example, the amplitudes of the noise signals, and the chest impedance are changed. By contrast, when chest compression is not performed, the amplitudes of the noise signals are not changed. Also when the patient breathes, the chest impedance is changed. However, the rate of the chest compression per minute is largely different from the respiratory rate of the patient (the spontaneous or artificial respiration rate of the patient). Based on the changes and the difference, the chest compression determiner 26 determines whether chest compression is performed or not.

If the chest compression determiner 26 determines that chest compression is not performed, the true ECG can be obtained by the above-described processes of the fundamental filter processor 25. By contrast, if it is determined that chest compression is performed, the true ECG is produced by the process of the chest compression noise removal processor 27. The contents of the process of producing the true ECG by the process of the chest compression noise removal processor 27 will be described later.

The electrocardiogram measurement electrodes 11 and the noise measurement electrodes 12 are placed (bonded) at predetermined positions of the patient, and connected to the measurers of the electrocardiogram analyzer main unit 20 through connectors attached to the ends of cords (cables) respectively extending from the electrodes 11, 12.

All the cords for the signals which can be measured by the respective electrodes may be collectively attached to one connector to constitute one electrode set. When the cords are collected to one connector, the operation by the operator (rescuer) can be simplified, and a rescue procedure can be rapidly performed. Alternatively, the cords for the signals which can be measured by the respective electrodes may be distributively attached to a plurality of connectors to constitute one electrode set. According to the configuration, a mode of the analyzer of the presently disclosed subject matter can be realized in an external apparatus such as a defibrillator, an electrocardiogram analyzer, an electrocardiogram displaying apparatus, or a biological information monitor, without changing the shapes of connectors, and the production cost can be suppressed.

Next, the true ECG produced by the chest compression noise removal processor 27 will be described.

In a defibrillator, defibrillation pads can be used as the electrocardiogram measurement electrodes 11, and information measured by the defibrillation pads, and that measured by the noise measurement electrodes 12 are combined with each other, thereby producing the true ECG.

Figure 2:
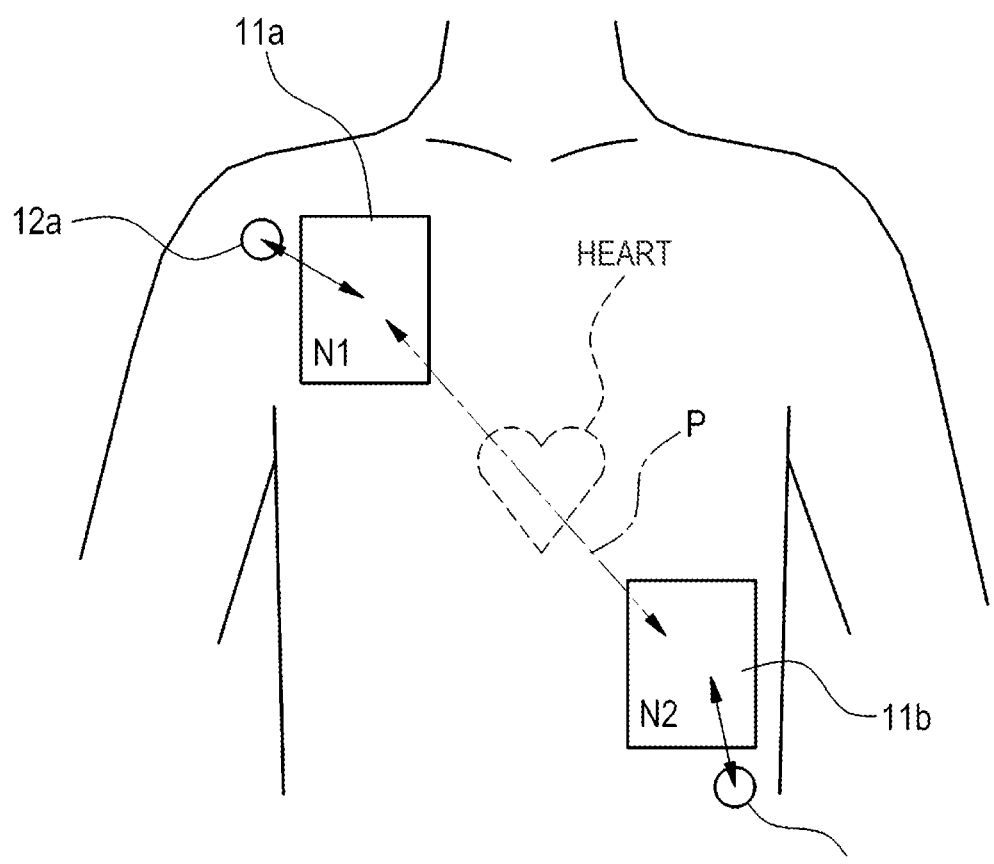
FIG. 2 is a diagram showing positions of electrodes for a defibrillator which are attached to the patient.

FIG. 2 shows the positions of the electrodes which are attached to the patient. A pair of defibrillation pads 11a, 11b are bonded to the subclavian region and the flank region, respectively, so as to interpose the heart therebetween. The defibrillation pads 11a, 11b are used for allowing a current of electric shock to flow through the patient, and also for measuring a change of the potential between the defibrillation pads 11a, 11b to measure the electrocardiogram of the patient. The lead Pad which is usually used in a defibrillator is measured as a change of the potential produced between the arrows P shown in FIG. 2, i.e., between the defibrillation pads 11a, 11b.

By contrast, noise measurement electrodes 12a, 12b for measuring the noise signals are bonded to the vicinities (an example of a predetermined position of the living body) of the defibrillation pads 11a, 11b, respectively. The noise signals are measured as changes of the potentials between the noise measurement electrodes and the defibrillation pads, i.e., potential changes between the noise measurement electrode 12a and the defibrillation pad 11a, and between the noise measurement electrode 12b and the defibrillation pad 11b. Hereinafter, the change of the potential which is produced between the arrows N1 shown in FIG. 2, i.e., between the noise measurement electrode 12a and the defibrillation pad 11a is defined as lead N1, and that of the potential which is produced between the arrows N2, i.e., between the noise measurement electrode 12b and the defibrillation pad 11b is defined as lead N2. Noise caused by chest compression enters the noise measurement electrodes 12a, 12b and also the defibrillation pads 11a, 11b. However, these electrodes are bonded to proximal positions, and therefore it can be deemed that there is no difference between the measurement times.

Figure 3A:
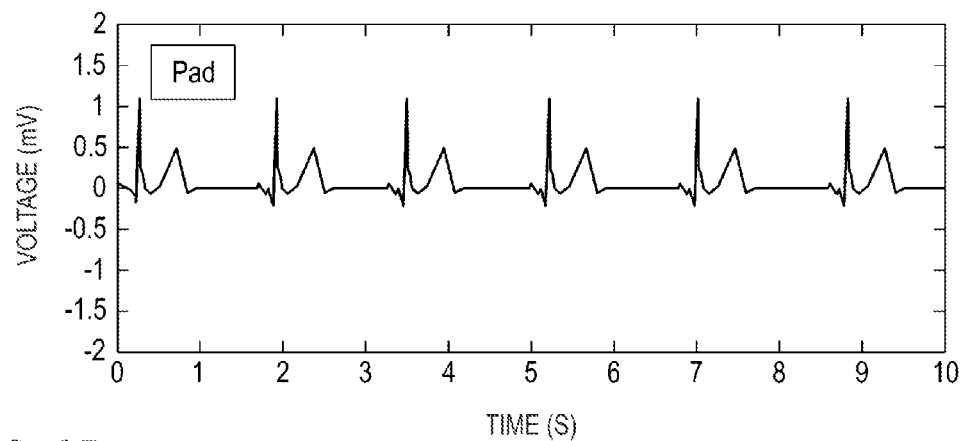
FIGS. 3A to 3C are diagrams showing signals measured at leads when chest compression is not performed.
Figure 3B:
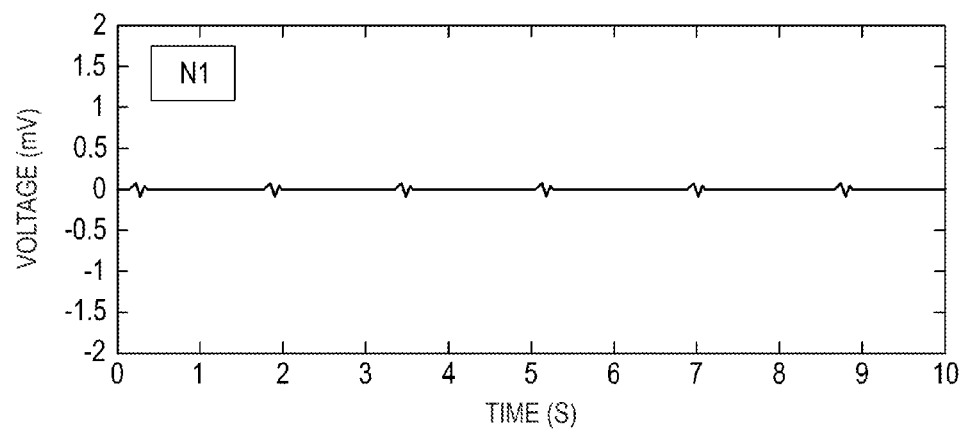
Figure 3C:
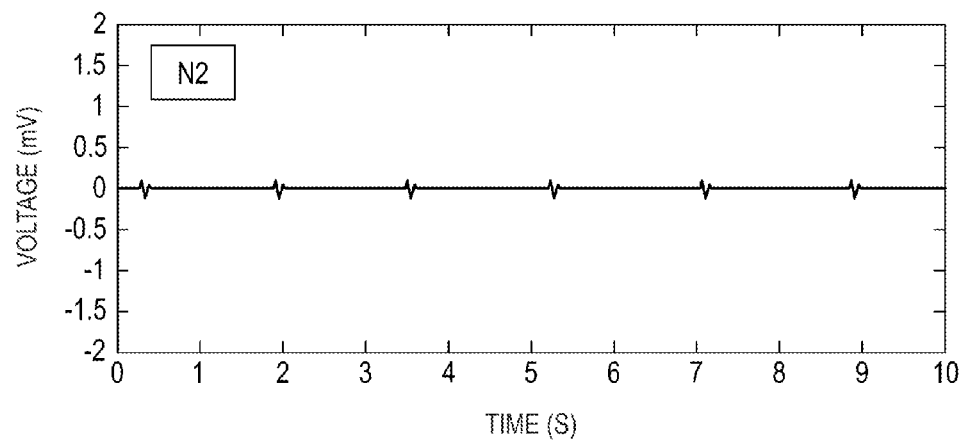

FIGS. 3A to 3C show signals which, in the measurement system shown in FIG. 2, are measured in the leads (lead Pad, lead N1, and lead N2) when chest compression is not performed on the patient, i.e., when noise is not produced.

As shown in FIGS. 3B and 3C, in the signals measured in leads N1 and N2, the amplitude of the potential appearing as an electrocardiogram is very low as compared with the signal (FIG. 3A) measured in lead Pad. This is caused by the positional relationships of the electrodes in which, unlike the case of lead Pad, the heart is not interposed between the electrodes (between the noise measurement electrode 12a and the defibrillation pad 11a, and between the noise measurement electrode 12b and the defibrillation pad 11b) in the case of lead N1 and lead N2, and the distances between the electrodes are sufficiently short.

Figure 4A:
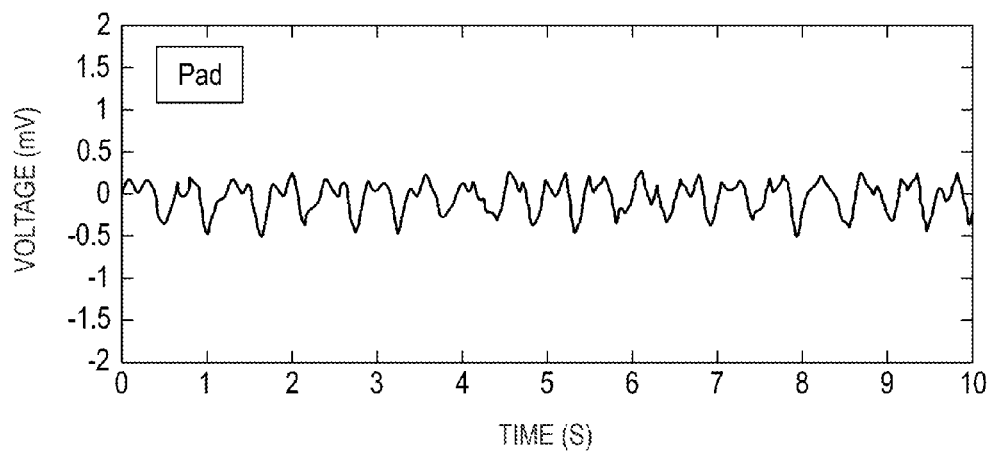
FIGS. 4A to 4C are diagrams showing signals measured at leads when chest compression is performed.
Figure 4B:
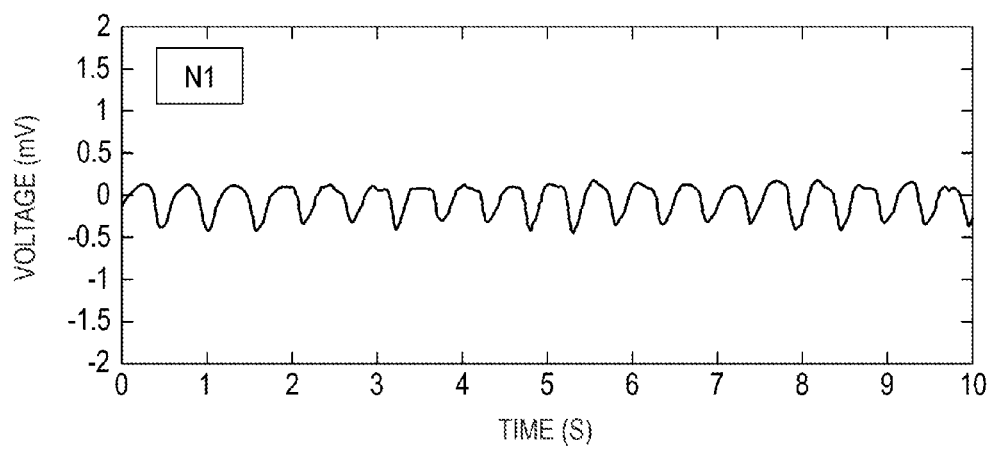
Figure 4C:
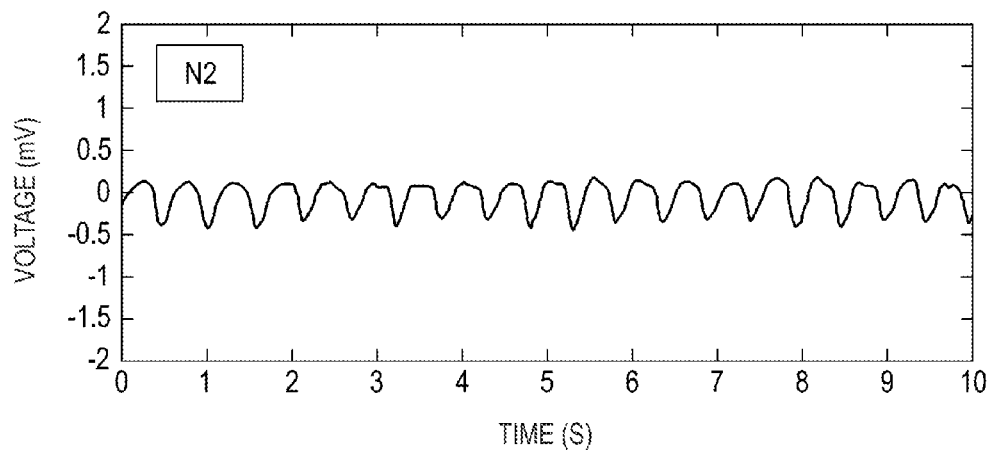

FIGS. 4A to 4C show signals which, in the measurement system shown in FIG. 2, are measured in the leads (lead Pad, lead N1, and lead N2) when chest compression is performed on the patient, i.e., when noise is produced.

As described above with reference to FIGS. 3B and 3C, the signals measured in leads N1 and N2 contain substantially no electrocardiogram signal. Therefore, it is possible to determine that the signals shown in FIGS. 4B and 4C are noise caused by chest compression.

From the above, therefore, the chest compression noise removal processor 27 can produce the true ECG signal by subtracting the signal of lead N1 measured by the noise measurement electrode 12a and the defibrillation pad 11a, or the signal of lead N2 measured by the noise measurement electrode 12b and the defibrillation pad 11b, from the lead Pad signal measured by the defibrillation pads 11a, 11b.

Figure 5A:
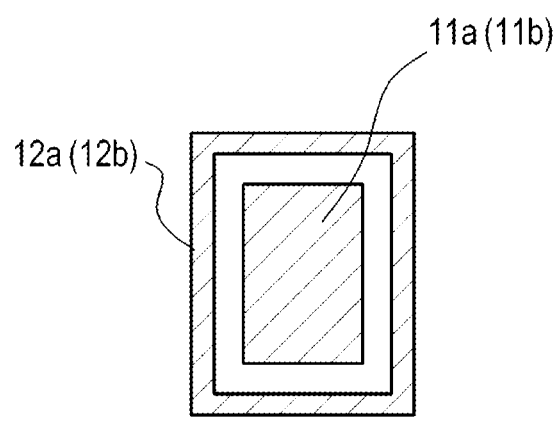
FIGS. 5A and 5B are views showing modifications of the forms of the electrodes.
Figure 5B:
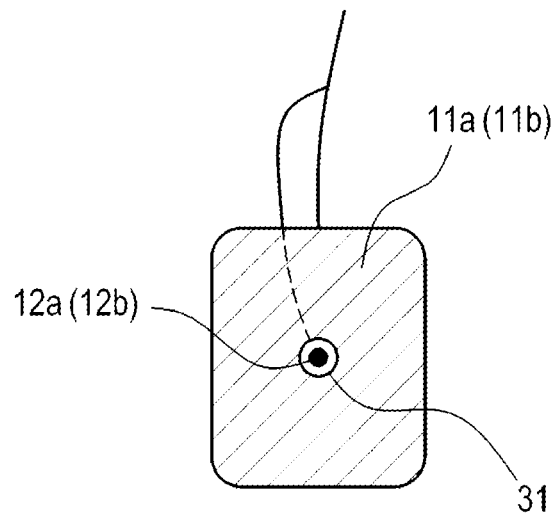

FIGS. 5A and 5B show Modification 1 of the defibrillation pads and noise measurement electrodes which are to be bonded to the patient. FIG. 5A shows one mode of the noise measurement electrode 12a (12b) which is bonded to the vicinity of the defibrillation pad 11a (11b). In the mode, as shown in the figure, the noise measurement electrode 12a (12b) is placed so as to surround the defibrillation pad 11a (11b).

FIG. 5B shows one mode in which the noise measurement electrode 12a (12b) is placed in the defibrillation pad 11a (11b). In the mode, as shown in the figure, an opening 31 is formed in the defibrillation pad 11a (11b), the noise measurement electrode 12a (12b) is placed in the interior (an example of the predetermined position of the living body) of the opening 31, and the pad and the electrode are bonded to the patient. Also in the configurations (FIGS. 5A and 5B), the noise signals can be measured, and the chest compression noise removal processor 27 can produce the true ECG signal.

Figure 6:
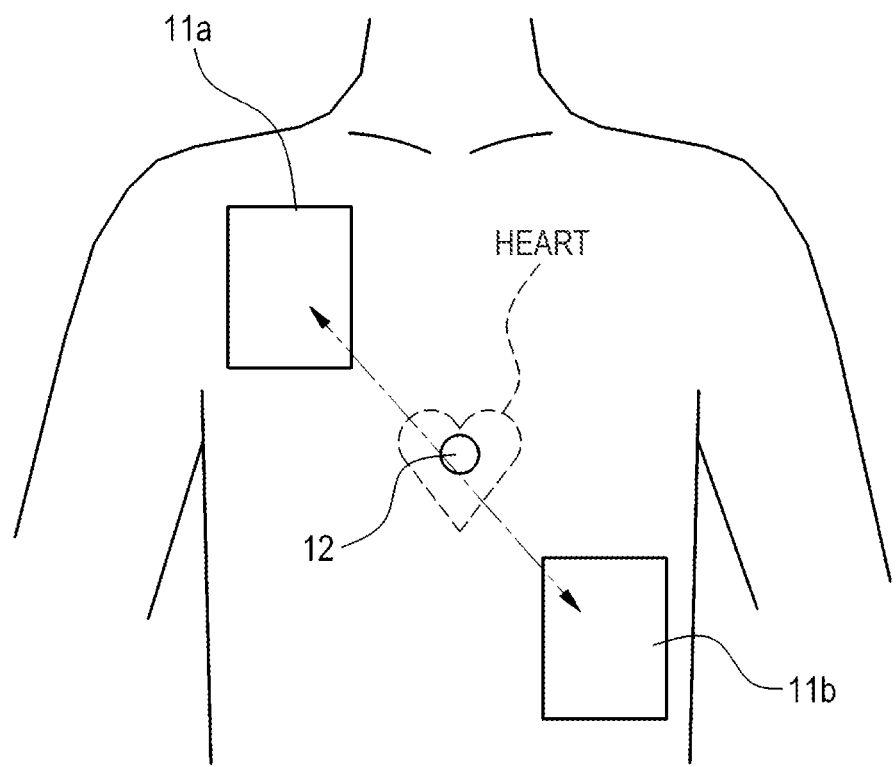
FIG. 6 is a diagram showing positions of electrodes which are bonded to the patient in a mode different from that of FIG. 2.

FIG. 6 shows another modification or Modification 2 of the defibrillation pads and noise measurement electrodes which are to be bonded to the patient. In the mode, as shown in the figure, the defibrillation pads 11a, 11b are bonded to positions interposing the heart, and the noise measurement electrode 12 is bonded to a chest compression portion which is between the pair of defibrillation pads 11a, 11b, i.e., an area above the heart (an example of a chest compression place). The noise measurement electrode 12 measures the induction of noise caused by chest compression. In this case, the pressure due to the chest compression is directly applied to the electrode, and therefore noise in which the amplitude is very high as compared with the electrocardiogram is measured. When electric signals of noise (chest compression) having such distinct characteristics are used, it is possible to select the optimum noise filter, and the true ECG signal can be produced by the chest compression noise removal processor 27.

In the above-described modes, the defibrillation pads are used as electrocardiogram measurement electrodes. Alternatively, for example, electrodes for measuring an electrocardiogram which are independent from defibrillation pads may be used while being placed in the vicinities of the defibrillation pads.

In the above-described modes, moreover, the defibrillation pads are used as electrodes for measuring an electrocardiogram, and the noise measurement electrode(s) which are bonded to the vicinities of the defibrillation pads are used as an electrode for measuring a noise signal. However, the presently disclosed subject matter is not limited to the mode. Alternatively, for example, the defibrillation pads may be used as an electrode for measuring noise signals, and electrodes which are bonded to the vicinities of the defibrillation pads may be used as an electrode for measuring an electrocardiogram. Also in the alternative, as in Modifications 1 and 2 which have been described with reference to FIGS. 5A and 5B, the electrocardiogram measurement electrodes may be placed so as to surround the defibrillation pads, or openings may be formed in the defibrillation pads, and the electrocardiogram measurement electrodes may be placed in the openings, respectively.

Figure 7:
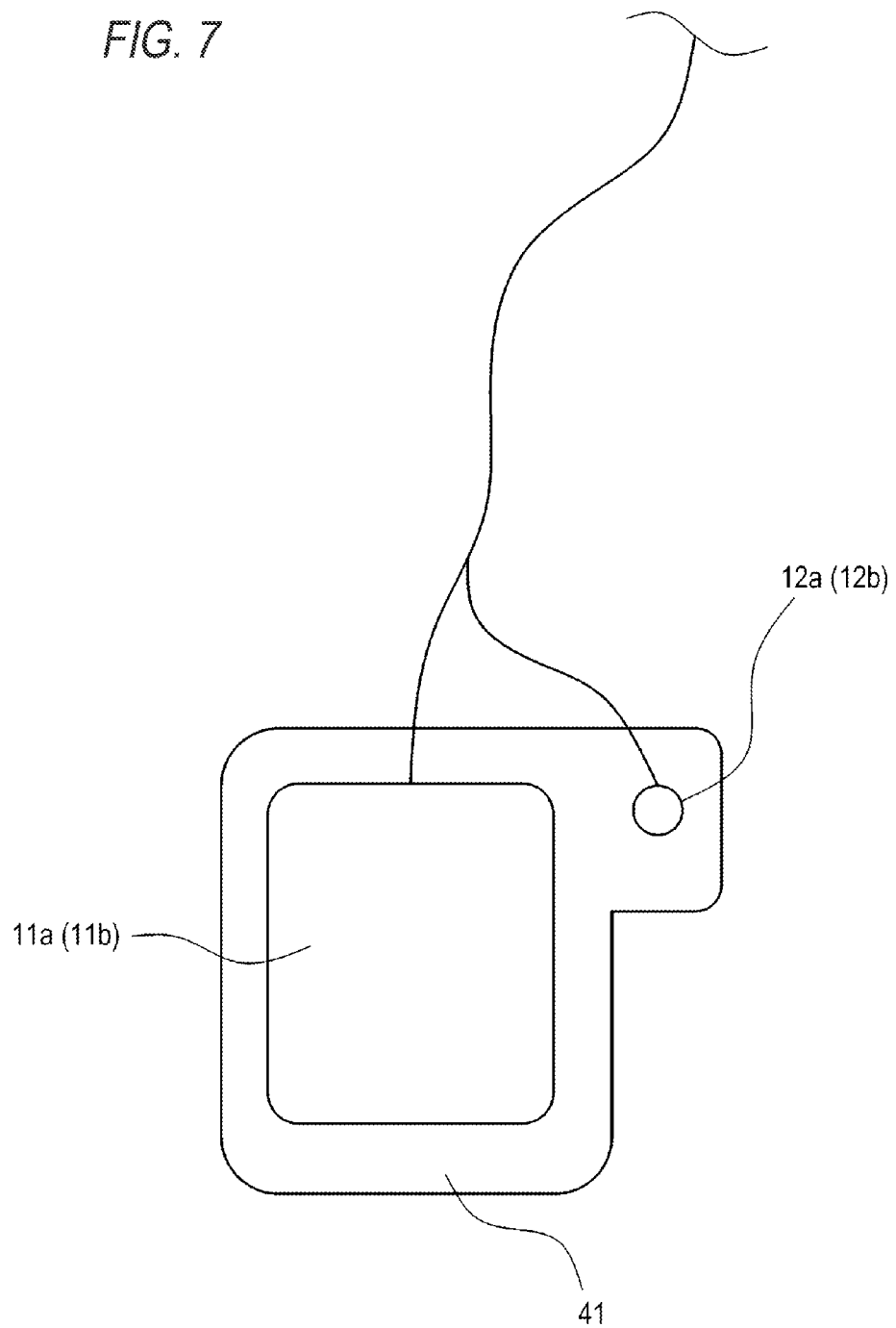
FIG. 7 is a diagram showing an example of electrodes in which an electrocardiogram measurement electrode and a noise measurement electrode are integrally formed.

In the above-described modes, moreover, the configuration where the noise measurement electrodes and the electrocardiogram measurement electrodes are separated into two or more bonding pads (sheets) is employed. However, the presently disclosed subject matter is not limited to the modes. As shown in FIG. 7, for example, a configuration where the defibrillation pad 11a (11b) and the noise measurement electrode 12a (12b) are attached to one bonding pad (sheet) 41 to be integrated into one electrode may be employed.

According to the configuration, the electrode(s) for measuring noise which are different from the electrodes (defibrillation pads) that are used for measuring an electrocardiogram in a defibrillator are bonded to the chest of the patient, noise signals caused by chest compression are positively measured (a disturbance itself which is caused between the electrodes and the skin is monitored), and the noise signals and an electrocardiogram signal are analyzed, whereby the influence of noise caused by chest compression can be effectively removed. Therefore, the electrocardiogram analysis (determination on whether application of defibrillation is required or not) of the defibrillator during chest compression can be performed more correctly, and the operator can perform a rapid rescue procedure.

Since the noise measurement electrodes are placed in the vicinities of the defibrillation pads, an electric signal having large noise components can be adequately measured as a noise signal. When the noise measurement electrode is placed between the defibrillation pads, a characteristic noise signal caused by chest compression can be measured and effectively removed.

In the configuration where an electrocardiogram is measured by electrodes which are disposed separately from the defibrillation pads, noise caused by chest compression can be removed. Also in the case where noise is measured by the defibrillation pads, when the noise signal and the electrocardiogram signal are analyzed, noise caused by chest compression can be removed.

In the configuration where an electrocardiogram measurement electrode and a noise measurement electrode are attached to one bonding pad (sheet) to be integrated with each other, the operator can correctly bond electrodes which are to be used in the electrocardiogram analysis, to the patient in the same procedure as the conventional one.

In the configuration where electrocardiogram measurement electrodes and noise measurement electrodes are separated into two or more sheets, existing defibrillation pads can used as they are as electrodes, and the cost can be suppressed.

When the chest impedance acquired from electrodes bonded to the patient is measured, it is possible to correctly determine on whether chest compression is performed or not.

Second Embodiment

As a second embodiment, an electrocardiogram analyzer which is used in a biological information monitor will be described. For example, the biological information monitor is a bedside monitor which detects biological information by means of a biological information detector attached to the patient, to display the detected biological information on a display. In the electrocardiogram analyzer 1 used in such a biological information monitor, an electrocardiogram monitor electrode 11A (11Ar, 11Al, 11Af) is used as an electrocardiogram measurement electrode. In the following description, the components which are identical or similar to those of the first embodiment are denoted by the same reference numerals, and their description will be omitted.

In the biological information monitor, information measured by the electrocardiogram monitor electrode 11A, and that measured by the noise measurement electrodes 12 are combined with each other, thereby producing the true ECG.

Figure 8:
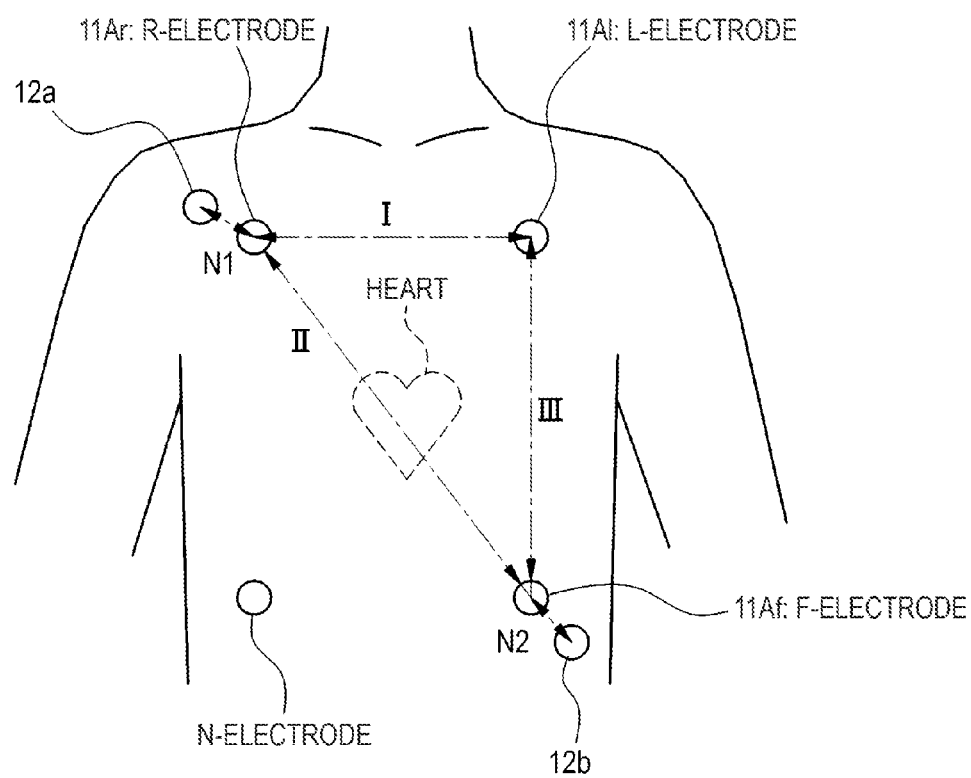
FIG. 8 is a diagram showing positions of electrodes for a biological information monitor which are attached to the patient.

FIG. 8 shows the positions of the electrodes for the biological information monitor which are attached to the patient.

The electrocardiogram monitor electrode 11A is configured by a set of plural electrodes such as three, six, or ten electrodes. The electrocardiogram monitor electrode 11A shown in FIG. 8 is configured by three electrodes, or an R-electrode 11Ar, an L-electrode 11Al, and an F-electrode 11Af. As shown in the figure, the R-electrode 11Ar is bonded below the right clavicle, the L-electrode 11Al below the left clavicle, and the F-electrode 11Af to the vicinity of the left flank.

According to the configuration, it is possible to measure an electrocardiogram due to a change of the potential between the R-electrode 11Ar and the L-electrode 11Al indicated by the arrow I in the figure (lead I), that due to a change of the potential between the R-electrode 11Ar and the F-electrode 11Af indicated by the arrow II (lead II), and that due to a change of the potential between the L-electrode 11Al and the F-electrode 11Af indicated by the arrow III (lead III). The leads I, II, and III are ones of the standard limb leads.

The noise measurement electrodes 12a, 12b are bonded to the vicinities of the R-electrode 11Ar and the F-electrode 11Af, respectively. According to the configuration, a noise signal is measured as a potential change between the noise measurement electrode 12a and the R-electrode 11Ar (lead N1), and that between the noise measurement electrode 12b and the F-electrode 11Af (lead N2).

Therefore, the chest compression noise removal processor 27 can produce the true ECG signal by subtracting the lead N1 signal measured by the noise measurement electrode 12a and the R-electrode 11Ar, or the lead N2 signal measured by the noise measurement electrode 12b and the F-electrode 11Af, from the lead II signal measured by the R-electrode 11Ar and the F-electrode 11Af.

Figure 9:
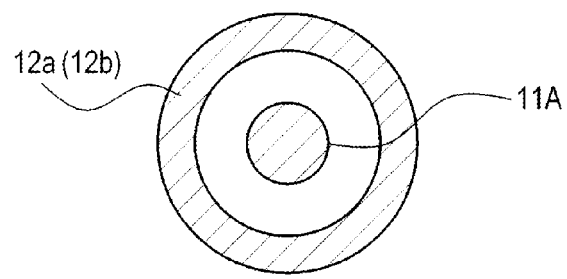
FIG. 9 is a diagram showing electrodes of a mode different from that of FIG. 8.

FIG. 9 shows a modification of the electrocardiogram monitor electrode and the noise measurement electrode. In the modification, as shown in the figure, the noise measurement electrode 12a (12b) is placed so as to surround the electrocardiogram monitor electrode 11A. Also in this configuration, a noise signal can be measured, and the true ECG signal can be produced by the chest compression noise removal processor 27.

Also in the second embodiment, similarly with the configuration of the first embodiment shown in FIG. 6, the noise measurement electrode 12 may be bonded to a chest compression portion which is between the R-electrode 11Ar and the F-electrode 11Af (in an area above the heart). Also in this case, the true ECG signal can be produced by the chest compression noise removal processor 27.

According to the configuration, also in a biological information monitor, the electrode for measuring noise which is different from the electrodes (defibrillation pads) that are used for measuring an electrocardiogram is bonded to the chest of the patient, a noise signal caused by chest compression is measured, and the noise signal and an electrocardiogram signal are analyzed, whereby the influence of noise caused by chest compression can be effectively removed. Therefore, the electrocardiogram analysis on the biological information monitor during chest compression can be performed more correctly. Consequently, the operator can perform a rapid rescue procedure, and similar effects as those in the case of the above-described defibrillator are achieved.

(Other Modes of Noise Removing Method)

Next, other modes of the noise removing method which is selected by the chest compression noise removal processor 27 will be described. In the first and second embodiments, the process in which, in the production of the true ECG, the lead N1 signal or the lead N2 signal is subtracted from the lead Pad signal (lead II signal) has been described. Alternatively, noise may be removed by performing one of the following filtering processes.

Figure 10A:
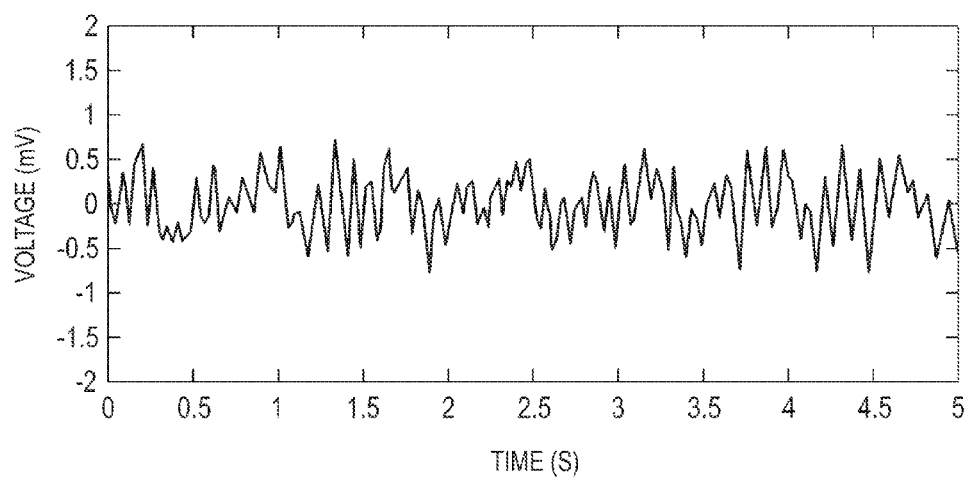
FIG. 10A is a view showing an electrocardiogram waveform in the case where chest compression is performed on a patient in ventricular fibrillation.
Figure 10B:
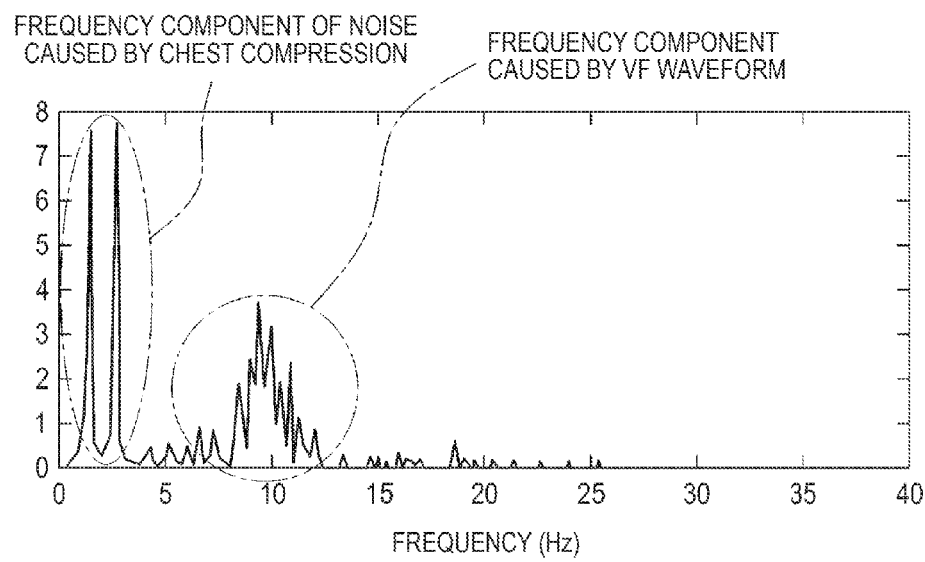
FIG. 10B is a view showing frequency components in the case where the electrocardiogram waveform shown in FIG. 10A is frequency analyzed.

For example, FIG. 10A shows an electrocardiogram waveform in the case where chest compression is performed on a patient suffering ventricular fibrillation (VF). FIG. 10B shows frequency components in the case where the electrocardiogram waveform shown in FIG. 10A is frequency analyzed. The frequency of ventricular fibrillation is relatively high. When a frequency analysis is performed, therefore, the frequency component of noise caused by chest compression is separated from that of the electrocardiogram (VF waveform) as shown in FIG. 10B. In order to determine whether the frequency components are separated from each other or not, frequency analyses are performed respectively on the electrocardiogram and the noise signal, and results of the analyses are compared with each other. If it is determined as a result of the frequency analyses that the frequency components are separated from each other, only the frequency band of the noise signal is removed from the electrocardiogram waveform, whereby the true ECG can be obtained. For example, the period of the chest compression may be obtained from the noise signal, and the filtering process may be performed based on the frequency of the chest compression (or an integer multiple of the frequency).

Figure 11A:
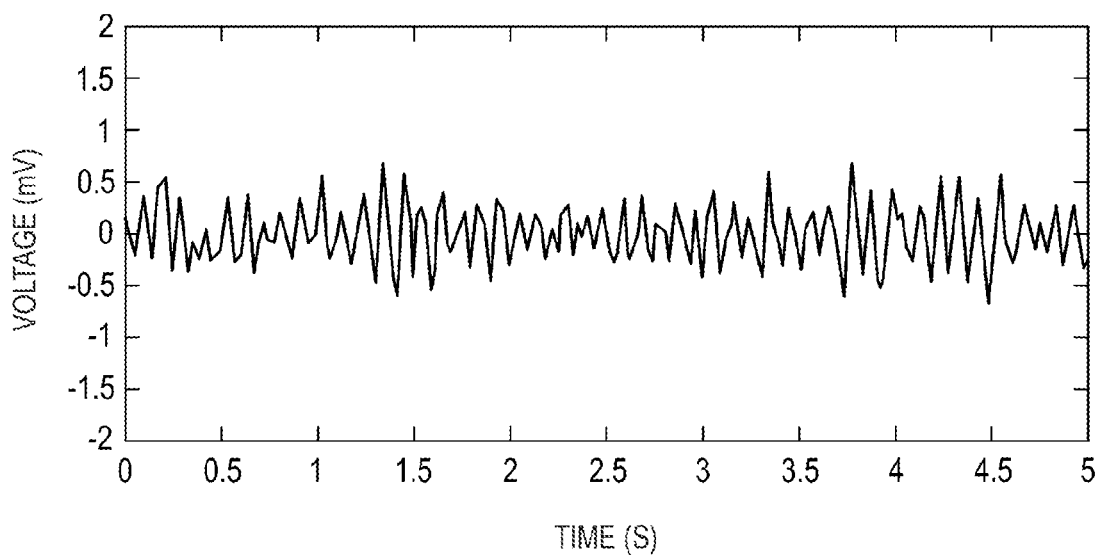
FIG. 11A is a view showing an electrocardiogram waveform in which the frequency band of a noise signal is removed from the electrocardiogram waveform shown in FIG. 10A.
Figure 11B:
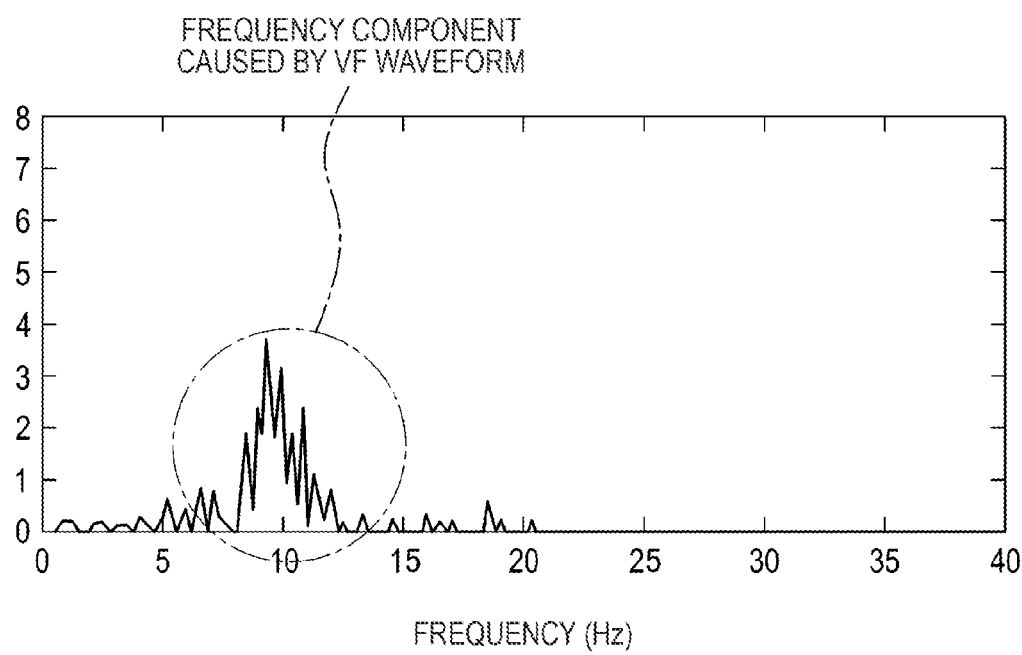
FIG. 11B is a view showing the frequency component in the case where the electrocardiogram waveform shown in FIG. 11A is frequency analyzed.

FIG. 11A shows a waveform in which the frequency band of the noise signal is removed by a notch filter from the electrocardiogram waveform shown in FIG. 10A, i.e., the true ECG. FIG. 11B shows the frequency component in the case where the electrocardiogram waveform shown in FIG. 11A is frequency analyzed. As apparent from the result of the frequency analysis, when comparing FIG. 11B with FIG. 10B, it can be determined that the noise signal caused by chest compression is removed.

Figure 12A:
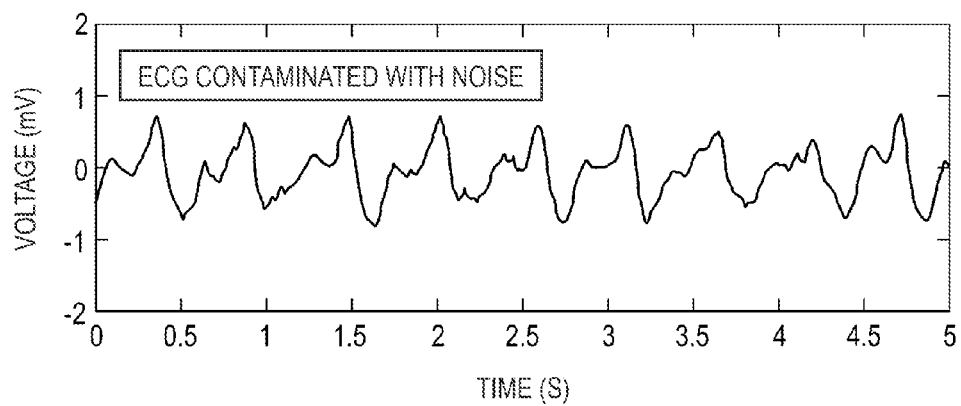
FIGS. 12A to 12C are views showing noise removal by the adaptive filtering process.
Figure 12B:
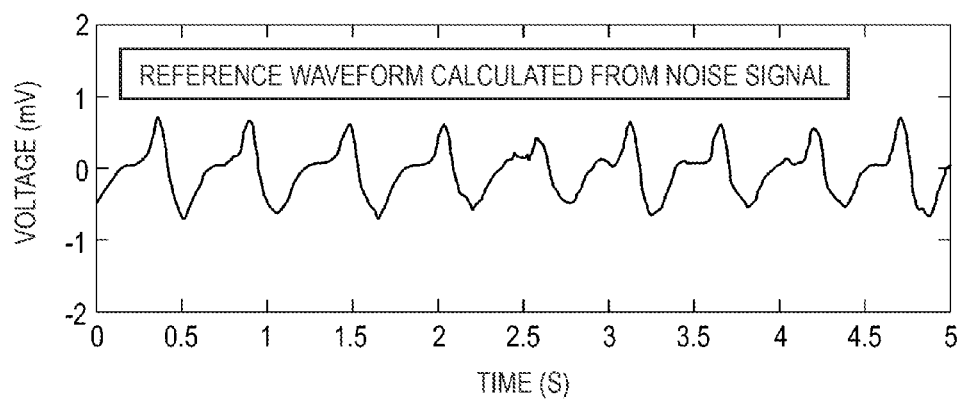
Figure 12C:
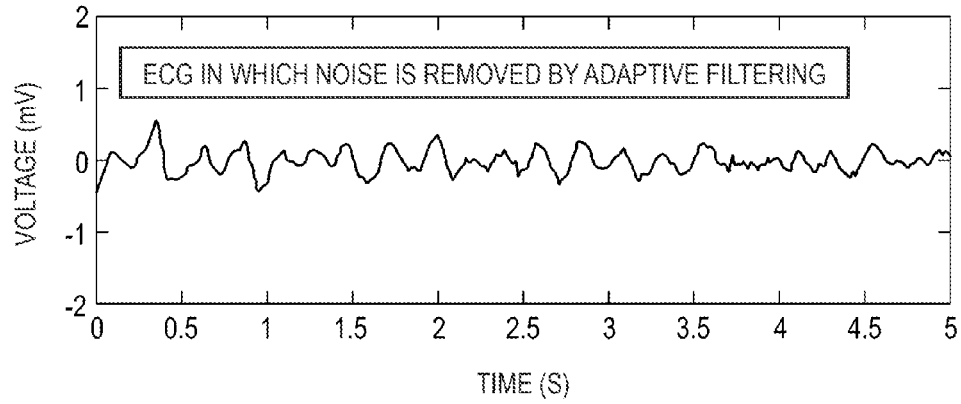

For example, FIGS. 12A to 12C show modes of removing noise by the adaptive filtering process in which noise signals are used as a reference.

FIG. 12A shows the signal of lead Pad in which ventricular fibrillation is contaminated with noise caused by chest compression, FIG. 12B shows a reference waveform indicating the difference between signals of leads N1 and N2 which are noise signals caused by chest compression, and FIG. 12C shows the true ECG in which noise is removed by an LMS adaptive filter that uses the difference between the signals of leads N1 and N2 as the reference for noise contaminating the electrocardiogram.

Optimization of the filter for noise is performed while changing the coefficient of the filter with time-variant noise such as the non-constant rate of chest compression. In other words, the frequency band to be removed is changed with the passage of time. Then, the filter coefficient is changed so that the result of the filtering process that is applied to the waveform (FIG. 11A) in which ventricular fibrillation and noise mixedly exist coincides with the waveform (FIG. 11B) in which only noise exists. As a result, the difference between them can be measured as the true ECG. When the noise signals are analyzed, it is possible to know that the rate of chest compression is not constant, and the rescuer may be informed of this.

For example, the number of noise measurement electrodes may be increased, a plurality of noise signals may be measured, and the filtering process may be performed on the noise signals and the electrocardiogram signal by independent component analysis, thereby removing noise.

When the noise signals and the electrocardiogram signal are analyzed, it is possible to select the optimum noise removing method from the plurality of above-described noise removing processes. In the case where the optimum noise removing method cannot be selected because of a reason such as that the frequency band of the electrocardiogram overlaps with that of the noise signals, the noise removal during chest compression may not be performed, and a waveform obtained by the filtering process using only the fundamental filter processor 25 may be set as the true ECG. This situation may be informed to the rescuer in the form of, for example, a text or voice message.

The measurers (the electrocardiogram measurer 21, the noise signal measurer 22, and the impedance measurer 23), the electrocardiogram analyzer 24 (the fundamental filter processor 25, the chest compression determiner 26, and the chest compression noise removal processor 27), and a transmitter which transmits the true ECG obtained in the electrocardiogram analyzer 24 to a defibrillator may be modularized into one signal processing component. The presently disclosed subject matter may be embodied by configuring an electrode set including the signal processing component, the electrocardiogram measuring electrodes 11, and the noise measuring electrodes 12, and having a noise removing function.

According to the configuration, the electrodes for measuring noise which are different from the electrodes that are used for measuring an electrocardiogram in a defibrillator or a biological information monitor are bonded to the chest of the patient, noise signals caused by chest compression are positively measured, and the noise signals and an electrocardiogram signal are analyzed, whereby the optimum noise removing method can be selected, and noise caused by chest compression can be reduced. In the case where the optimum noise removing method cannot be selected, the cause of this situation can be informed to the rescuer. Therefore, a subsequent appropriate procedure can be performed, and the situation can be improved.

According to an aspect of the presently disclosed subject matter, a disturbance itself which is caused between an electrode and the skin is monitored, and therefore noise caused by chest compression can be effectively removed. Consequently, the electrocardiogram analyzer more accurately analyzes an electrocardiogram, and the operator can perform a rapid procedure.

What is claimed is:

1. An electrocardiogram analyzer comprising:
one set of electrocardiogram measurement electrodes;
one or more noise measurement electrode which includes an electrode placed in a vicinity of corresponding one of the electrocardiogram measurement electrodes;
a measurer which is configured to measure an electrocardiogram signal acquired by the electrocardiogram measurement electrodes, and a noise signal acquired between the electrode included in the noise measurement electrode and the corresponding one of the electrocardiogram measurement electrodes; and
an electrocardiogram extraction analyzer which is configured to extract a noise-removed electrocardiogram in which noise is removed, based on the electrocardiogram signal and the noise signal.

2. The electrocardiogram analyzer according to claim 1, wherein the set of electrocardiogram measurement electrodes are a pair of defibrillation pads adapted to apply electric shock.

3. The electrocardiogram analyzer according to claim 1, wherein the noise measurement electrode includes a pair of defibrillation pads adapted to apply electric shock.

4. The electrocardiogram analyzer according to claim 1, wherein the noise measurement electrode is disposed in an opening formed in corresponding one of the electrocardiogram measurement electrodes.

5. The electrocardiogram analyzer according to claim 1, wherein the noise measurement electrode is placed between the set of electrocardiogram measurement electrodes.

6. The electrocardiogram analyzer according to claim 1, wherein the noise signal is based on an impedance which is acquired when a carrier current is applied between the noise measurement electrode and the electrocardiogram measurement electrodes.

7. The electrocardiogram analyzer according to claim 1, wherein a period of chest compression is obtained from the noise signal, and a filtering process is performed based on a frequency of the chest compression.

8. The electrocardiogram analyzer according to claim 1, wherein an adaptive filtering process in which the noise signal is used as a reference is performed.

9. The electrocardiogram analyzer according to claim 1, wherein a filtering process is performed on the noise signal and the electrocardiogram signal by independent component analysis.

10. The electrocardiogram analyzer according to claim 1, wherein cables for the electrocardiogram measurement electrodes, and at least one cable for the noise measurement electrode are attached to one connector, and the connector is connectable to the measurer.

11. The electrocardiogram analyzer according to claim 1, wherein cables for the electrocardiogram measurement electrodes, and at least one cable for the noise measurement electrode are distributively attached to two or more connectors, and the connectors are connectable to the measurer.

12. The electrocardiogram analyzer according to claim 1, wherein one of the electrocardiogram measurement electrodes, and the noise measurement electrode are disposed on one sheet, and are connectable to the measurer.

13. The electrocardiogram analyzer according to claim 1, wherein the electrocardiogram measurement electrodes, and the noise measurement electrode are distributively disposed on at least two sheets, and are connectable to the measurer.

14. The electrocardiogram analyzer according to claim 1 which is incorporated in a defibrillator.

15. An electrode set which is to be connected to an external apparatus, the electrode set comprising:
one set of electrocardiogram measurement electrodes;
one or more noise measurement electrode which includes an electrode placed in a vicinity of corresponding one of the electrocardiogram measurement electrodes;
a measurer which is configured to measure an electrocardiogram signal acquired by the electrocardiogram measurement electrodes, and a noise signal acquired between the electrode included in the noise measurement electrode and the corresponding one of the electrocardiogram measurement electrodes;

an electrocardiogram extraction analyzer which is configured to extract a noise-removed electrocardiogram in which noise is removed, based on the electrocardiogram signal and the noise signal; and a transmitter which is configured to transmit the noise-removed electrocardiogram to the external apparatus.

* * * * *